(12) United States Patent
Van Buskirk et al.

(10) Patent No.: US 11,052,385 B2
(45) Date of Patent: Jul. 6, 2021

(54) PHOTOCATALYTIC SURFACE SYSTEMS

(71) Applicants: Peter C. Van Buskirk, Brookfield, CT (US); Maryam Golalikhani, Trumbull, CT (US); Melissa A. Petruska, Newtown, CT (US); Jeffrey F. Roeder, Brookfield, CT (US)

(72) Inventors: Peter C. Van Buskirk, Brookfield, CT (US); Maryam Golalikhani, Trumbull, CT (US); Melissa A. Petruska, Newtown, CT (US); Jeffrey F. Roeder, Brookfield, CT (US)

(73) Assignee: Sonata Scientific LLC, Danbury, CT (US)

(*) Notice: Subject to any disclaimer, the term of this patent is extended or adjusted under 35 U.S.C. 154(b) by 0 days.

(21) Appl. No.: 16/212,663

(22) Filed: Dec. 6, 2018

(65) Prior Publication Data

US 2019/0168204 A1 Jun. 6, 2019

Related U.S. Application Data

(60) Provisional application No. 62/595,261, filed on Dec. 6, 2017, provisional application No. 62/760,428, filed on Nov. 13, 2018.

(51) Int. Cl.
*B01J 21/06* (2006.01)
*B01J 23/745* (2006.01)
(Continued)

(52) U.S. Cl.
CPC ............. *B01J 35/004* (2013.01); *A61L 9/205* (2013.01); *B01J 21/063* (2013.01); *B01J 23/745* (2013.01);
(Continued)

(58) Field of Classification Search
CPC . B01J 21/04; B01J 21/06; B01J 21/063; B01J 21/066; B01J 21/08; B01J 35/004; B01J 35/0013; B01J 35/0073; B01J 35/008; B01J 35/023; B01J 23/745; B01J 37/0209; A61L 9/205
See application file for complete search history.

(56) References Cited

U.S. PATENT DOCUMENTS 5,658,841 A * 8/1997 Tanaka ................... B01J 35/002
502/242
5,703,002 A * 12/1997 Towata ................... B01J 35/002
502/328

(Continued)

*Primary Examiner* — Cam N. Nguyen
(74) *Attorney, Agent, or Firm* — Gregory Stauf

(57) ABSTRACT

The Invention describes integration of photocatalytic materials into composite surfaces in order to achieve antimicrobial properties. Aspects of the invention include types of photocatalytic materials and methods to achieve long lifetimes, high durability and mechanical robustness, for application to medical and sanitary uses, among others. In particular, the invention describes production of photocatalytic islands on a porous support substrate, and various methods to prevent full contact of a matrix material with the photocatalytic islands on the porous support substrate when forming the photocatalytic composite. Reducing the area of contact between the matrix material and the photocatalytic material improves the lifetime of the photocatalytic materials employed in the photocatalytic composite.

20 Claims, 17 Drawing Sheets

(51) Int. Cl.
  *B01J 35/00* (2006.01)
  *B01J 35/02* (2006.01)
  *B01J 37/02* (2006.01)
  *A61L 9/20* (2006.01)

(52) U.S. Cl.
  CPC ......... *B01J 35/008* (2013.01); *B01J 35/0013* (2013.01); *B01J 35/0073* (2013.01); *B01J 35/023* (2013.01); *B01J 37/0209* (2013.01)

(56) References Cited

U.S. PATENT DOCUMENTS

| | | | | |
|---|---|---|---|---|
| 5,780,380 A * | 7/1998 | Endoh | .................. | B01J 35/004 502/300 |
| 6,217,999 B1 * | 4/2001 | Zhang | .................. | B01J 13/02 427/213.34 |
| 6,949,284 B2 * | 9/2005 | Yoshihara | .................. | G02B 1/111 428/212 |
| 7,521,394 B2 * | 4/2009 | Xie | .................. | B01J 21/063 423/610 |
| 8,283,277 B2 * | 10/2012 | Seeber | .................. | B82Y 30/00 502/159 |
| 8,871,670 B2 * | 10/2014 | Seebauer | .................. | B01J 27/14 502/300 |
| 9,855,549 B2 * | 1/2018 | Gao | .................. | B01J 35/006 |
| 2002/0016250 A1 * | 2/2002 | Hayakawa | .................. | C03C 17/23 502/5 |
| 2002/0160913 A1 * | 10/2002 | Sangiovanni | .................. | B01J 37/036 502/350 |
| 2002/0187082 A1 * | 12/2002 | Wu | .................. | C02F 1/725 422/139 |
| 2007/0184975 A1 * | 8/2007 | Yi | .................. | B01J 23/06 502/343 |
| 2009/0026063 A1 * | 1/2009 | Skiles | .................. | B01D 53/62 204/157.3 |
| 2010/0051443 A1 * | 3/2010 | Lee | .................. | B01J 35/0013 204/157.15 |
| 2010/0137130 A1 * | 6/2010 | Book | .................. | C09D 5/1687 502/218 |
| 2010/0297447 A1 * | 11/2010 | Tadakuma | .................. | B01J 35/002 428/403 |
| 2011/0312080 A1 * | 12/2011 | Hatton | .................. | C04B 38/04 435/289.1 |
| 2012/0010068 A1 * | 1/2012 | Zhao | .................. | B01J 35/004 502/1 |
| 2012/0189681 A1 * | 7/2012 | Macedo Tavares | ... | A01N 25/18 424/408 |
| 2013/0153483 A1 * | 6/2013 | Morazzoni | .................. | B01J 35/1071 210/263 |
| 2013/0237409 A1 * | 9/2013 | Sambandam | .................. | B01J 37/08 502/184 |
| 2014/0179512 A1 * | 6/2014 | Landry | .................. | B01J 27/0573 502/1 |
| 2014/0256534 A1 * | 9/2014 | Gao | .................. | B01J 23/66 502/5 |
| 2014/0262806 A1 * | 9/2014 | Jennings | .................. | B01J 35/004 205/340 |
| 2015/0111725 A1 * | 4/2015 | Van Buskirk | .................. | B01J 21/063 502/200 |
| 2015/0376441 A1 * | 12/2015 | Guldin | .................. | C09D 5/006 428/220 |
| 2018/0243727 A1 * | 8/2018 | Khan | .................. | B01J 37/0248 |
| 2019/0111657 A1 * | 4/2019 | Aizenberg | .................. | C09C 1/0084 |
| 2020/0101440 A1 * | 4/2020 | Petruska | .................. | B01J 35/1023 |

* cited by examiner

PHOTOCATALYTIC SURFACE SYSTEMS

CROSS REFERENCE TO RELATED APPLICATIONS

This application is a U.S. Utility application taking priority from U.S. Provisional application No. 62/595,261 "Photocatalytic Surface Systems", filed Dec. 6, 2017, and from U.S. Provisional Patent Application No. 62/760,428 "Monolithic Composite Photocatalysts", filed Nov. 13, 2018 both herein incorporated by reference.

BACKGROUND OF THE INVENTION

References

Bachmann, et al., "A Practical, Self-Catalytic, Atomic Layer Deposition of Silicon Dioxide," *Angew. Chem. Int. Ed.* 2008, 47, 6177-6179.
Bedwell, W., et al., (2016) U.S. Pat. No. 9,259,513. Washington, D.C.: US Patent and Trademark Office.
Cargnello M. et al., "Solution-Phase Synthesis of Titanium Dioxide Nanoparticles and Nanocrystals" *Chem. Rev.* 2014, 114, 9319.
Christofordis K. C. et al., "Role of $TiO_2$ Morphological Characteristics in EVOH—$TiO_2$ Nanocomposite Films: Self-Degradation and Self-Cleaning Properties" *RSC Advances* 2013, 3, 8541.
Dinh C.-T. et al., "Shape-Controlled Synthesis of Highly Crystalline Titania Nanocrystals" *ACS Nano* 2009, 3, 3737.
Djouiai B. et al., "Role of DNA Repair and Protective Components in *Bacillus subtilis* Spore Resistance to Inactivation by 400 nm Blue Light." *Appl. Environ. Microbiol.* 2018, 84, 01604.
Hiller, D., et al., "Low Temperature Silicon Dioxide by Thermal Atomic Layer Deposition: Investigation of Materials Properties," *J. Appl. Phys.,* 2010, 107, 064314.
Jones, F. N., Nichols, M. E., Socrates, P. P. (2017). Organic Coatings: Science and Technology (Fourth Edition). Hoboken, N.J.: John Wiley and Sons, Inc.
Kubacka A. et al., "Boosting $TiO_2$-Anatase Antimicrobial Activity: Polymer-Oxide Thin Films" *Applied Catalysis B: Environmental* 2009, 89, 441.
Li X. et al., "Mechanism of Photodecomposition of $H_2O_2$ on $TiO_2$ Surfaces under Visible Light Irradiation" *Langmuir* 2001, 17, 4118.
Nakano R. et al., "Broad Spectrum Microbicidal Activity of Photocatalysis by $TiO_2$" *Catalysts* 2013, 3, 310.
Oh, J., et al., "Etch Behavior of ALD $Al_2O_3$ on HfSiO and HfSiON Stacks in Acidic and Basic Environments," *J. Electrochem. Soc.,* 2011, 158, D217-D-222.
Puronen, R., et al., "Implementing ALD in MEMS Applications," *ECS Trans.,* 2007, 11, 3-14.
Setlow B. et al., "Role of DNA Repair in *Bacillus subtilis* Spore Resistance." *J. Bacteriol.* 1996, 1783486, 3486.
Szymanski T. et al., U.S. Pat. No. 5,733,840. Washington, D.C.: US Patent and Trademark Office.
Venkatadri, R., Peters, R. W., "Chemical Oxidation Technologies: Ultraviolet Light/Hydrogen Peroxide, Fenton's Reagent, and Titanium Dioxide-Assisted Photocatalysis", HAZARDOUS WASTE & HAZARDOUS MATERIALS Volume 10, Number 2, 1993
Visai L. et al., "Titanium Oxide Antibacterial Surfaces in Biomedical Devices" *Int. J. Artif. Organs* 2011, 9, 929.
Williams, K., et al., "Etch Rates for Micromachining Processing—Part II," *J. Microelectromechanical Systems,* 2003, 12, 761-778.
You Y. S. et al., "Deactivation and Regeneration of Titania Catalyst Supported on Glass Fiber in the Photocatalytic Degradation of Toluene" *Korean J. Chem. Eng.* 2003, 20, 58.
Zhou, B., et al., (199) U.S. Pat. No. 5,876,614. Washington, D.C.: US Patent and Trademark Office.
Kemmell, M., "Atomic Layer Deposition of Nanostructured $TiO2$ Photocatalysts via Template Approach," Chem. Mater., 2007, 19, 1816-1820.
Liu., X., et al., (2012) United States Patent Application No US2011/0142725A1, Washington, D.C.: U.S. Patent and Trademark Office.
Pore et al, "Atomic layer deposition of photocatalytic $TiO2$ thin films from $TiF4$ and $H2O$, Dalton Transactions, 2008, 6467-6474.
Pore, V., et al., "Atomic layer deposition of $TiO2-xNx$ thin films for photocatalytic applications," J. Photochemistry and Photobiology, 2006, 177, 68-75.
Toshiaki, A., et al., (2007) United States Patent Application No US2007/0031681 A1, Washington, D.C.: U.S. Patent and Trademark Office.
Wang, X., et al., "A Mesoporous Pt/$TiO2$ Nanoarchitecture with Catalytic and Photocatalytic Functions," Chem. Eur. J, 2008, 11, 2997-3004.
Weimer, A., (2012) United States Patent Application No US2012/0201860, Washington, D.C.: U.S. Patent and Trademark Office.
Willette, C., (2007) United States Patent Application No US2007/0059225 A1, Washington, D.C.: U.S. Patent and Trademark Office.
Miklos, D. B., Remy, C., Jekel, M., Linden, K. G., Drewes, Jö. E., Hübner, U., "Evaluation of advanced oxidation processes for water and wastewater treatment—A critical review", Water Research (2018), doi: 10.1016/j.watres.2018.03.042. Bolton, James R., Collins, James, Advanced Oxidation Handbook, American Water Works Association, Denver, 2016.
Christoforidis, Konstantinos C. et al., "Role of $TiO2$ morphological characteristics in EVOH—$TiO2$ nanocomposite films: self-degradation and self cleaning properties", RSC Advances (20130 3, 8451-8550.
Sjogren, J. C, Sierka, R. A, "Inactivation of phage MS2 by iron-aided titanium dioxide photocatalysis", Applied and Environmental Microbiology, 1994, 60(1) pp. 344-7
PaolaVillegas-Guzman, P., Giannakis, s., Torres-Palmaa, R. A., Pulgarin, C., "Remarkable enhancement of bacterial inactivation in wastewater through promotion of solar photo-Fenton at near-neutral pH by natural organic acids", Applied Catalysis B: Environmental, 205, pp. 219-227

The present invention relates to novel photocatalytic surface systems that incorporate improved photocatalytic materials in a matrix that provides cohesion and mechanical strength. The resulting surfaces possess properties that include bactericidal, viricidal, sporicidal, hardness, abrasion resistance, and chemical resistance. It also relates to providing photocatalytic solid surfaces incorporating photocatalysts in a matrix with improved resistance to photocatalytic-induced degradation of the matrix. Matrix materials are comprised of organic polymers, inorganic compounds or mixtures. The photocatalytic materials will be dispersed in a liquid precursor or particulate solid precursor that are used to form a solid surface, film or article. It also relates to methods to form the photocatalytic surface systems, including extrusion, spray coating, and 3-d additive manufacturing. It also relates to fluid cleaning formulations for the subject high durability surfaces that provide a specific chemistry that complements the photocatalytic and antimicrobial activity of the surface.

It also relates to novel systems applications and implementations that utilize the subject materials systems for mitigation of microbes, volatile organic materials and other environmental contamination. It also relates to in-vivo applications such as implants, where the photocatalytic illumination is transmitted through the flesh, via fiber optics, or by implanted light sources.

We are faced with increasing threats from harmful microbes, including bacteria, viruses, spores and bacteria-comprised biofilms. Healthcare Associated Infections (HAI) are a major problem that threatens life and increases costs of healthcare. The CDC estimates that in the U.S. there are 1.7 million HAIs annually, contributing to 99,000 deaths. One primary transmission mode for these infections involves contact with contaminated surfaces, where bacteria and viruses can reside for days or even weeks on touch surfaces near the patient. MRSA, *C. Difficile*, MDRA and *Staphylococcus* are particularly dangerous and stubborn contagions that may reside on surfaces close to a patient. Many types are difficult to attack with antibiotics, and antibiotic resistance is spreading to Gram-negative bacteria that can infect people outside the hospital.

Outside the healthcare world, there are a similar and increasing range of opportunistic mass-infections as evidenced by recent Norovirus outbreaks on cruise ships. These outbreaks may be spread by viruses, bacteria and spores that propagate both airborne and from surfaces to surface.

It is well known that many standard disinfecting regimens (typically liquids comprised of bleach or hydrogen peroxide) may leave a residual contagion on a surface, which is known as "Bioburden". Bioburden is comprised of biofilm or planktonic species residing at a surface that is nominally 'clean'. Its presence may be due to failure of hospital staff to follow standard procedures, species with exceptional physical, chemical and biological robustness, or a combination of those. There are several disinfectant treatments that are receiving wide attention as ways to augment liquid treatments. UV-C radiation, ozone and disinfectant vapors or mists are known to be very effective but are highly hazardous and are only viable when a hospital room has been vacated.

Antimicrobial, or 'self-sterilizing' surfaces are highly desirable to complement standard cleaning. They act continuously, and ideally, they should have a high killing efficiency for a broad range of bacteria, viruses and spores, and be non-toxic to humans. Silver and copper containing surfaces are the most widely investigated, but these have shortcomings including toxicity, cost and questions about long term efficacy because of the adaptation of bacteria.

Titanium dioxide is the archetypal photocatalyst due to its highly oxidizing properties when irradiated by UV light, physical robustness, insolubility in water, low cost, low toxicity and other attributes. Photocatalysis using titanium dioxide (titania, $TiO_2$) has received huge interest for purifying gases and fluids, in particular air and aqueous fluids, via oxidizing chemical reactions at a surface, via creation of electron-hole pairs.

A wide variety of titania-based materials, doping schemes, and physical configurations have been proposed to enhance and utilize photocatalysis at $TiO_2$ surfaces, although so far there has not been widespread adoption of the technology for purification of air, fluids or surfaces. The inventors of the present invention believe that several technical and economic factors have reduced the utility, effectiveness, and commercial viability of photocatalytic air purification systems.

Photocatalysis is typically achieved by a low or medium pressure UV lamp, or in some cases a Xenon lamp, irradiating the front surface of a ceramic- or powder-based titania surface, i.e., from the direction of the medium that is targeted to be purified. UV LEDs have also been employed, although these devices typically have very short product lifetimes and are unreliable. Photocatalysis utilizing titanium dioxide is typically excited by illumination in the UV or near UV 240-400 nm spectral region, which is hazardous to humans, more technologically complicated and more expensive than visible-light-based illumination sources.

The chemical activation at the surface of a photocatalyst originates with the formation of electron-hole pairs that arise from optical stimulation. Activation at the surface typically has a finite lifetime that is limited by illumination and recombination of electron-hole pairs. Mitigation of these effects has been investigated primarily via chemical modification of the titania particles, although there has been no consensus in technical approach for manufacturing practical photocatalyst materials and systems.

The photocatalytic materials of the present invention, such as those described above, and others, may be formed in a variety of configurations also identified in the present invention, thereby enabling a range of photocatalytic antimicrobial surfaces and devices.

The photocatalytic materials and illumination schemes of the subject invention may be incorporated in a wide range of devices in order to effect or enhance antimicrobial characteristics of surfaces. These materials may be directly applied to solid surfaces of interest or mixed with flexible polymeric materials that are subsequently applied to surfaces or formed into those products directly.

Those antimicrobial products that may incorporate the subject inventions include, but are not limited to, doorknobs, pens, smartphone screens, computer screens and keyboards, escalator rails, elevator buttons, countertops, hospital 'high touch surfaces' such as bed hand rails, medical instrumentation, medical instruments, catheters, in-vivo implantable medical hardware and structures, etc.

It is evident that these materials, when incorporated on consumer, commercial and medical products, will be exposed to considerable abrasion, mechanical impact and chemical agents used to clean and sanitize these products on a daily basis. Incorporation of the subject photocatalytic materials in polymeric matrices is highly desirable due to their widespread use and cost advantages. There are specific technical problems with incorporation of photocatalytic materials in such organic hosts, because the reactive oxygen species can react with and deteriorate the organic material in contact with those photoactive surfaces. The present invention provides several novel means to prevent such contact and deterioration.

The subject invention may be embodied in the following examples that are by no means restrictive, but intended to illustrate the invention. It will be clear that the described invention is well adapted to achieve the purposes described above, as well as those inherent within. The citation of any publication is for its disclosure prior to the filing date and should not be construed as an admission that the present invention is not entitled to antedate such publication by virtue of prior invention. Numerous other changes may be made which will readily suggest themselves to those skilled in the art and which are encompassed both in the spirit of the disclosure above and the appended claims.

SUMMARY OF THE INVENTION

The present invention relates to novel photocatalytic materials, and to antimicrobial surfaces that incorporate those materials in a polymer or inorganic matrix. It also relates to soluble nanocrystals of the photocatalytic material. It also relates to novel methods to prevent chemical interaction of the photocatalytic materials with the polymer matrix. It also relates to novel photocatalytic enhancing liquid cleaning formulations for those surfaces.

DETAILED DESCRIPTION OF THE INVENTION AND PREFERRED EMBODIMENTS THEREOF

Figure 1:
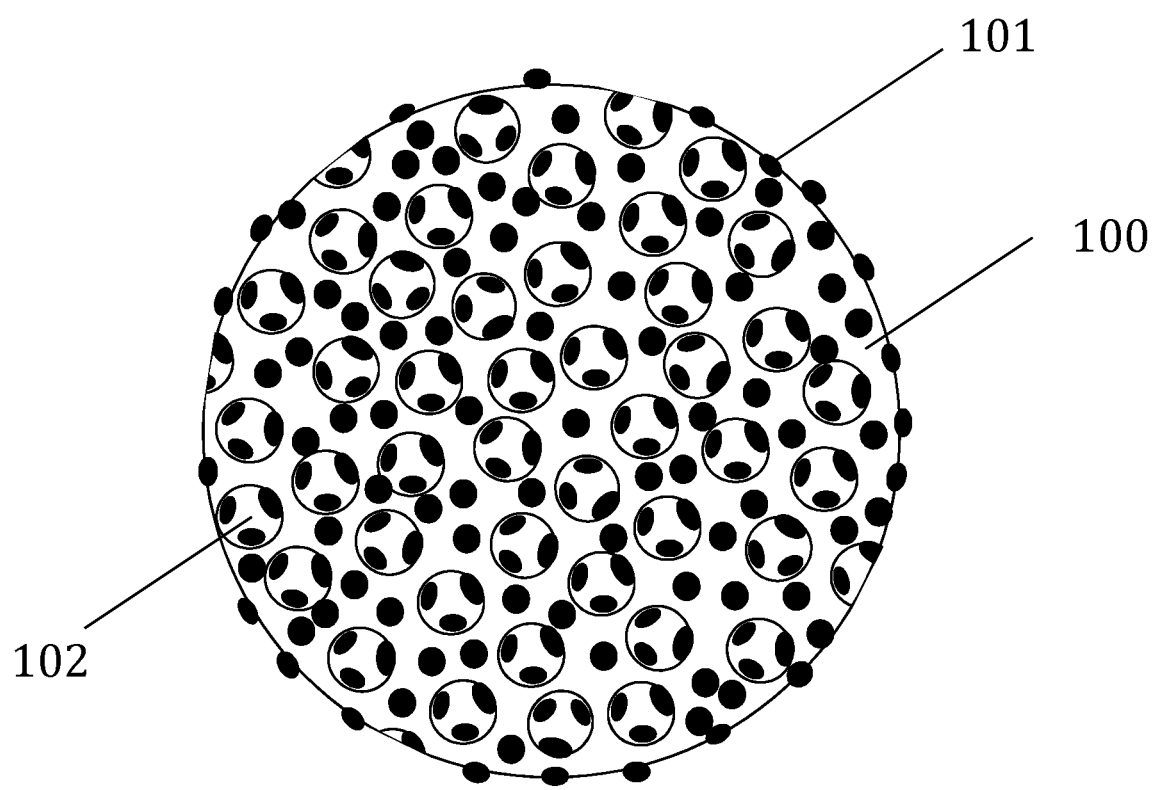
FIG. 1 shows a schematic of a monolithic composite photocatalyst.

One aspect of the invention relates to monolithic composite photocatalysts comprising thin layers or islands of $TiO_2$ or modified $TiO_2$ photoactive species on porous supports that have high transmission of UV-A and visible illumination for highly efficient use of the material. (FIG. 1). The porous support 100 will also enhance VOC activity, promoting complete mineralization (i.e., decomposition) of target environmental contaminants. The $TiO_2$ ceramic materials 101 will have a high content of the anatase crystal phase to optimize photocatalytic surface chemistry and activity and a surface rich in hydroxyl groups. They may be dispersed within pores of the support 102 as well as on the surface. Other modified titanium dioxide compositions include those doped with rare earth oxides, (e.g., $TiO_2$—$CeO_2$ or any other lanthanide or combination thereof), with transition metals or salts of transition metals (e.g., Co, W, V, W, Zr, Cu, Fe, Cr, Ag), with non-metals including N, S, and F, or the aforementioned materials combined with metal nanoscale or microscale metal particles at the titania surface, e.g., Pt, Pd, Ag, Au, Cu, Fe, etc. Modified $TiO_2$ materials, including but not limited to the stoichiometric $TiO_2$ formulations, will be referred to as "titania" in the description and claims of this invention. These compounds and combinations of compounds, formed on porous optically non-absorbing supports, will be referred to as 'monolithic composite photocatalysts' in the description and claims of this invention. For the purposes of this invention, optically non-absorbing means less than 10% absorbance at the specified photocatalytic illumination wavelength through a 4 mm bed. The photocatalytic illumination wavelength may range from UV-A through 550 nm, i.e., 360 nm-550 nm. The subject photocatalytic materials are also useful for illumination at 250 nm to 360 nm wavelength. These thin layers or islands may also be particularly active when formed on high surface area or high porosity substrates, for example those which have BET surface area in the range of 0.05-250 $m^2/g$ determined from $N_2$ adsorption isotherms collected at 77 K, pore size in the range 2 nm-200 microns, and pore volume in the 0.1-1.0 cc/g range. Substrate compositions can include alumina, silica, zeolites, titania, zirconia, and silicalites that exhibit transparency (>90%) at the wavelength of illumination.

The subject porous photocatalytic substrates may be powdered or pulverized as needed for incorporation into other organic or inorganic matrix materials. The matrix materials may be derived from liquid or solid precursors.

Monolithic composite titania photocatalysts are prepared using wet impregnation techniques in which known quantities of the photocatalyst precursor solutions are added to the support. The supported titania is dried and then calcined to achieve the desired crystalline phase. Repeated impregnation-drying steps can be used to increase the amount of photocatalyst on the solid support. Titania precursors useful for this impregnation synthesis include titanium ethoxide, titanium propoxide, titanium isoproproxide, titanium t-butoxide, titanium nitrate, titanium oxalate, ammonium titanyl oxalate, titanium sulfate, titanium oxysulfate, titanium citrate, and ammonium titanium (IV) bis(ammonium lactato) dihydroxide. Alkoxides, nitrates, sulfates, acetates, and oxalates of the dopant metal additive can be used. Solvents for impregnation include water, ethanol, propanol, isopropanol, dilute sulfuric acid, and dilute nitric acid.

The surface functionality of the supported titania, namely the number of hydroxyl groups on the surface, can be enhanced using wet etching techniques, including peroxide, acid, or base treatments. The number of hydroxyl groups has been shown to correlate with the photocatalytic performance of the photocatalyst.

Another aspect of the invention is the regeneration of the monolithic composite titania photocatalysts. Photocatalyst fouling can occur through a number of pathways, including the adsorption of incompletely mineralized by-products onto the titania material. Supported catalysts can be regenerated for re-use using visible light and water. Alternatively, heat treatments can be used to drive off the adsorbed species. Surfaces can be re-primed with hydroxyl groups using wet etching techniques, including peroxide, acid, or base treatments.

It will be understood to those practiced in the art of photocatalytic materials that the subject invention will also be useful and directly applicable to photo-electrochemical (PEC) cells, super-hydrophilic surfaces, antimicrobial surfaces, self-cleaning surfaces and other related applications of titania-based materials.

Another aspect of the invention relates to colloidal nanocrystals of $TiO_2$ or modified $TiO_2$ ceramics capped with solubilizing ligands which render the nanocrystals soluble in a range of solvents. The preferred NC sizes are in the range of 2-15 nm, and applicable solvents include nonpolar varieties (e.g., toluene, hexane), polar solvents (e.g., ethanol, propanol, ethyl acetate), or water.

Whereas a number of researchers have fabricated nanocrystals of titania, they are typically suspended in liquid media and will eventually agglomerate and/or settle out of the suspension. The present invention is to fabricate such NCs with organic or inorganic ligands affixed during early stages of processing, thereby preventing agglomeration. Such ligand systems may be subsequently exchanged for others during processing or partially removed, and these ligands will enable facile manipulation of the nanocrystals, including the direct incorporation of the NC-containing solution into a matrix described below.

Figure 2:
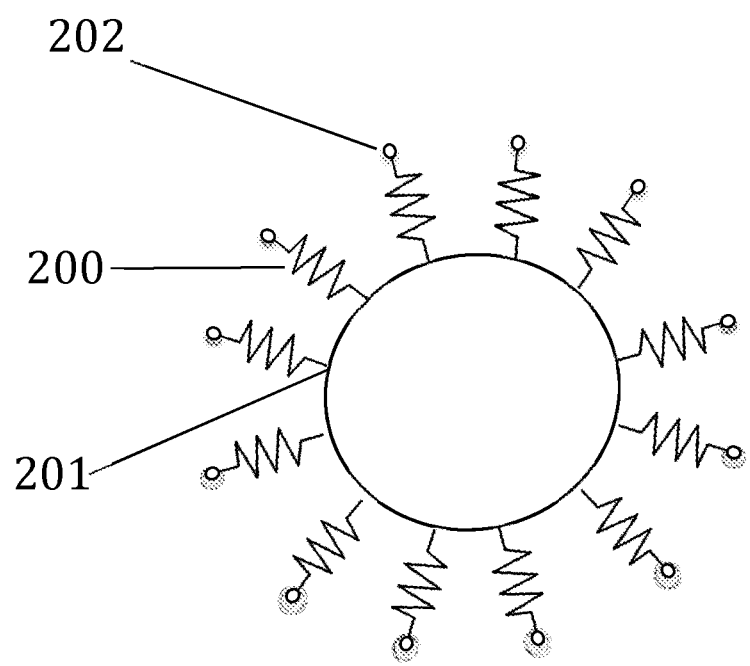
FIG. 2 shows a schematic of a soluble nanocrystal with surface functionalizing groups.

Titania NCs can be prepared following a variety of wet chemical and solvothermal approaches. Depending on the reaction conditions (e.g., temperature, reaction time, solvents, ligands, etc.), a variety of shapes (spheres, rods, bipyramids, etc.), crystalline phases, sizes, and solubilities can be achieved. Soluble, non-aggregated titania nanocrystals (FIG. 2) are attained by incorporating ligands 200 that can coordinate to the surface of the nanocrystals 201 during growth (FIG. 2). These ligands prevent particles from aggregating, passivate surface defects, and allow for nanocrystal solubility in a variety of solvents. Ligand removal and exchange processes can take place in solution using precipitation strategies that require solvents for which the NCs are insoluble and the ligands are soluble. The precipitated nanocrystals are separated from the excess ligands through filtration or centrifugation and then redissolved in a suitable solvent. The precipitating solvent is added again, and the process is repeated until the desired surface coverage is obtained. Non-coordinating functional groups 202 can be used to tether the NCs to different matrix materials.

A related aspect of the invention describes fabrication methods to form the photocatalytic nanocrystal materials with optical absorption shifted to longer wavelengths (e.g., >400 nm) in order to utilize visible light LEDs to stimulate the photocatalytic effect. Other modified titanium dioxide compositions include those doped with rare earth oxides, (e.g., $TiO_2$—$CeO_2$ or any other lanthanide or combination thereof), with transition metals or salts of transition metals (e.g., Co, W, V, W, Zr, Cu, Fe, Cr, Ag), with non-metals including N, S, and F, or the aforementioned materials combined with metal nanoscale or microscale metal particles at the titania surface, e.g., Pt, Pd, Ag, Au, Cu, Fe, etc.

One aspect of the invention is the fabrication of photocatalytic surface systems and articles by incorporation of the subject soluble photocatalytic nanocrystal materials into a solid forming liquid matrix material that may be otherwise engineered to achieve additional desirable properties such as mechanical hardness, abrasion resistance, high transparency for photocatalytic illumination, visible or other electromagnetic radiation, magnetic properties, hydrophilicity, hydrophobicity, specific nano, micro or macroscopic topographies or shapes, etc.

One objective of the present invention is to provide antimicrobial properties to the coating using photocatalytic particles that produce reactive oxygen species (ROS) while avoiding degradation of the matrix due to the production of ROS at the matrix-particle interface. Fabrication steps to produce desirable structures are described below.

Alternatively powdered or pulverized mesoporous photocatalytic materials may also be incorporated in the subject inorganic or organic matrix materials. The matrix materials may be derived from liquid or solid precursors.

The matrix may be either inorganic or organic based. Examples of inorganic matrix materials are silica, alumina, and titania film materials. Organic matrices may be rigid materials such as rigid epoxies, polyurethanes, polycarbonates, polypropylenes, thermoplastics (e.g., nylon, PET), or pliable materials such as silicones or flexible epoxies. Organic matrix materials may also be comprised of combinations of these constituent materials. These materials may be dispensed as liquids or as solids. They may optionally be cured at elevated temperature or by exposure to UV light. Curing temperatures may range from 50-300° C. UV light may comprise UV-A, UV-B or UV-C.

Titania nanocrystals can be incorporated into a liquid-derived matrix using ligand exchange approaches. Exchanging the ligands on the surface of the nanocrystals will affect their solubility. Suitable ligands are selected based on the presence of functional groups that can coordinate to the nanocrystal surface (for titania nanocrystals, appropriate coordinating groups include alkoxy silane groups, phosphonic acids, carboxylic acids, and hydroxyl groups) and the termination group of the ligand (e.g., alkyl chains will render the nanocrystals soluble in nonpolar solvents). Suitable choices are not limited to triethoxylmethylsilane, triethoxyhexylsilane, triethoxyoctylsilane, octylphosphonic acid, hexylphosphonic acid and the like. Surface capping agents with a multi-functional compound of the formula $X.sub.x$—$(Z.sub.n)$—$Y.sub.y$ where X can be a sulfonic acid group (—$SO_3H$), an alkoxysilane group (—$Si(OX)$), a phosphonic acid (—$PO_3H_2$) group, a phosphine oxide (—PO) group, a hydroxyl group (—OH), or a carboxylic acid group (—COOH), x is an integer and is one or more, Z can be a hydrocarbon group, such as an alkyl group, an aryl group or an alkylaryl group, a polyether group, an ethylene oxide group, a propylene oxide group or a mixture thereof, n can generally be from 1 to 20, Y can be a hydroxyl (—OH) group, a carboxylic acid (—COOH) group, a sulfonic acid (—$SO_3H$) group, a phosphonic acid group (—$PO_3H_2$) group, or an alkoxysilane group (—Si(OX)) and y is an integer and is one or more can also be selected to facilitate incorporation into the matrix material.

For example, the multi-functional compound can include the combination of functionalities such as phosphonic acid-hydroxyl, phosphine oxide-hydroxyl, phosphonic acid-carboxylic acid, phosphine oxide-carboxylic acid, phosphonic acid-sulfonic acid, phosphine oxide-sulfonic acid, and phosphine oxide-phosphonic acid. Exemplary materials include, but are not limited to 4-phosphonobutyric acid, 4-hydroxybutylphosphonic acid, tris(hydroxypropyl)phosphine oxide, bis(dibutyl)(hydroxypropyl)phosphine oxide and the like.

Functional groups that do not coordinate to the nanocrystal surface are free to participate in condensation reactions with, for example, silica sol-gel precursors, or to bind to functionalities on monomer or polymer backbones as a method for uniformly distributing the nanocrystals throughout the matrix. Alternatively, the ligands can be chosen merely to impart solubility in the desired matrix material (e.g., polyurethanes).

Minimal amounts of coordinating ligands can be used to manipulate the nanocrystals into the desired matrix without completely covering the titania surface, allowing for reactive oxygen species to form at the surface to provide antimicrobial activity. Alternately, once embedded in the matrix, UV light treatments can be used to remove coordinating ligands adjacent to the titania surface through photocatalytic oxidation reactions, particularly when carboxylic acids and hydroxyl groups are used as the coordinating functionality. Wet etchants can also be used to create photoactive titania surfaces, including peroxide, acids, and bases.

Titania nanocrystal loading levels within the matrix material can be varied to achieve optimum performance (0.1-20 wt %). Ligand-based, soluble nanocrystals can be well-dispersed in the desired matrix, allowing charges to be effectively distributed throughout. The liquid matrix-titania composite can be deposited as films using a variety of techniques, including spin-coating, dip coating, spray coating, drop coating, roll-to-roll printing, and the like. Once deposited, the films can be cured by elevated temperature or UV light exposure. After curing, the titania surfaces optionally can be activated with wet-etchants, including peroxide, to enhance the surface hydroxyl groups necessary for forming the reactive oxygen species critical for photocatalysis. These etchants can be applied during routine cleaning/wipe-down cycles as an approach for reinvigorating and optimizing the photocatalytic efficiency.

One embodiment involves the deposition of photocatalyst-containing matrix materials onto solid surfaces, including those found in hospital rooms and operating rooms as well as on instrumentation, which includes surgical instruments, catheters, and other non-implantable items that have the potential to carry bacteria and viruses. Composites of photocatalysts with suitable inorganic or organic matrix materials, including sol-gel, spin-on-glass, siloxanes, polyurethanes, and other appropriate materials, can be deposited onto these substrates using a variety of techniques, including spraying, printing, spin-coating, dip-coating, additive manufacturing (i.e. 3-d printing), extrusions, spin coating, printing, incorporation on fibers, etc. This matrix can also be deposited on glass surfaces or plastic coatings (e.g., 150 μm polyethylene terephthalate (PET)) that will be applied to the surface of interest as a second step. The matrix must meet the durability requirements for effective functioning, including robustness. In one example, an inorganic polymer matrix such as a silica sol-gel is used. Silica sols can withstand degradation from reactive oxygen species. Curing temperatures are low, at less than 120° C., which allow compatibility with plastic substrates. Titania sols have been successfully deposited onto biomedical devices for photocatalytic antimicrobial testing.

It is expected that $TiO_2$ (Mohs hardness=6) nanoparticles will provide high durability. The mechanical properties of a composite structure containing photocatalytic material may be enhanced using additional components that are mixed into the composite. If needed, additional materials, e.g., $Al_2O_3$ (Mohs hardness=9), may be added. Very small amounts of $Al_2O_3$ (<0.5%) have a large effect on wear resistance of polymer films like epoxies. Additional additives that can enhance the mechanical properties of the films include silica, refractory oxides, carbides and nitrides. Illustrative combinations include, but are not limited to, aluminum oxide into a photocatalytic particle/$SiO_2$ matrix, aluminum oxide into a photocatalytic particle/silicone matrix, photocatalytic particle/epoxy matrix, silicon oxide into a photocatalytic particle/polyurethane matrix, or silicon oxide into a photocatalytic particle/silicone matrix or photocatalytic particle/epoxy matrix. Other such mechanical property modifying particles may include transformation toughened alumina, hafnia, or zirconia. Alternatively, other particles that increase toughness may be added, e.g., a polymer particle in an inorganic matrix containing photocatalytic particles.

The incorporation of traditional titania photocatalyst particles (e.g., bulk photocatalysts, i.e., pure $TiO_2$ or $TiO_2$ modified by elemental additions) that are not coated with ligands into an organic matrix material leads to degradation of the organic matrix from the production of reactive oxygen species. Particle coating approaches described in the present invention may be used to overcome this problem.

Previous work has shown that UV light (365 nm) can directly degrade organic polymers, but photo-degradation of the polymer is not an expected outcome with visible light. However, photocatalytic solids in a polymer can degrade the polymer via reactive oxygen species that oxidize adjacent regions of the polymer. Reactive oxygen species, e.g., .OH, $.O_2^-$, can break C—C bonds in a polymer chain, which then results in degradation of the structural integrity and mechanical properties of the polymer. The incorporation of photocatalysts into film matrix materials that contain organic species, including, e.g., siloxanes (silicone), epoxies, and polyurethane, must also be accomplished without degrading the organic components to a degree that affects the film wear-resistance during photocatalytic activity (i.e., the generation of reactive oxygen species). Dispersing low concentrations of the photocatalyst homogeneously throughout the film (accomplished by achieving high solubility through, e.g., shear mixing) is one current approach for preserving film properties. However, some minimum photocatalyst concentration is required for providing the desired antimicrobial properties. While these approaches attempt to minimize degradation in the near-term, long-term degradation remains a problem and further, the amount of photocatalyst that may be incorporated to achieve optimal antimicrobial performance is also limited. Therefore, strategies that reduce, diminish, or minimize oxidation of the polymer effectively reduce degradation of the polymer matrix, thus preserving its mechanical properties.

The present invention incorporates several methods to prevent deleterious oxidizing reactions at the interface between the photocatalytic particle and an organic, e.g., polymeric matrix host material. These approaches include monolithic composite photocatalysts, a blocking shell layer on a support to prevent infiltration of the liquid matrix precursor into pores, a core-shell geometry that may be employed at the photocatalytic particle surface, different size particles with respect to photocatalytic film thickness, and choice of the optimum matrix polymer to resist or retard degradation. In the case of monolithic composite photocatalysts, thin layers or islands of titania are fixed to a porous support, providing antimicrobial properties, while limiting the amount of photoactive titania directly in contact with the matrix. Stated differently, the areal density of titania on the porous support is less than that of titania as a homogeneous particle. The surface coverage of photocatalyst on the porous support may be in the range of 10-90%. Monolithic composite photocatalysts can be prepared in various form factors, including as powders. Powders added to coating matrix precursors can be milled (e.g., ball mill, jet mill, etc.) and/or shear-mixed in the coating precursor to reduce particle size and improve dispersions. Monolithic composite photocatalysts can also be prepared as beads that are several hundred nanometers to several hundred microns in diameters. These beads can be added directly to a matrix or pulverized and used as powders.

Monolithic composite photocatalysts may be combined with either organic or inorganic matrix materials. Matrix materials that have high hardness values will impart good wear resistance to the film. An advantage of monolithic composite photocatalysts is that in one embodiment the $TiO_2$ is supported on alumina, which imparts additional wear resistance to the matrix. In another embodiment where the $TiO_2$ is supported on silica, the silica (Mohs hardness=7) also imparts additional wear resistance to the matrix.

A further advantage to the use of monolithic composite photocatalysts in polymer matrix is that they have a lower density of $TiO_2$ at the particle-matrix interface compared to pure $TiO_2$, which decreases the degradation of the matrix in the case of polymeric (organic) matrix materials.

Figure 3:
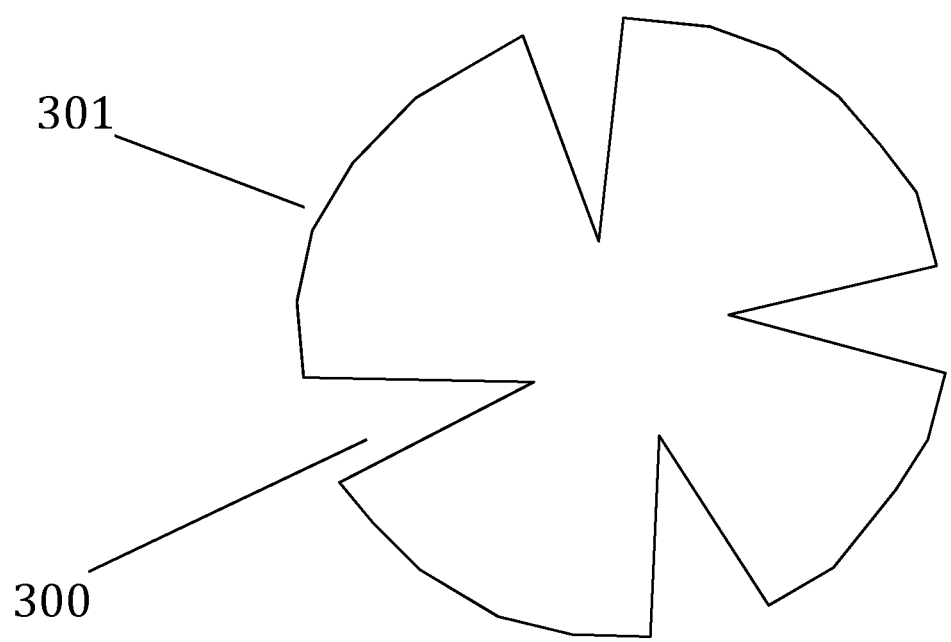
FIG. 3 shows a schematic of a porous support.
Figure 4:
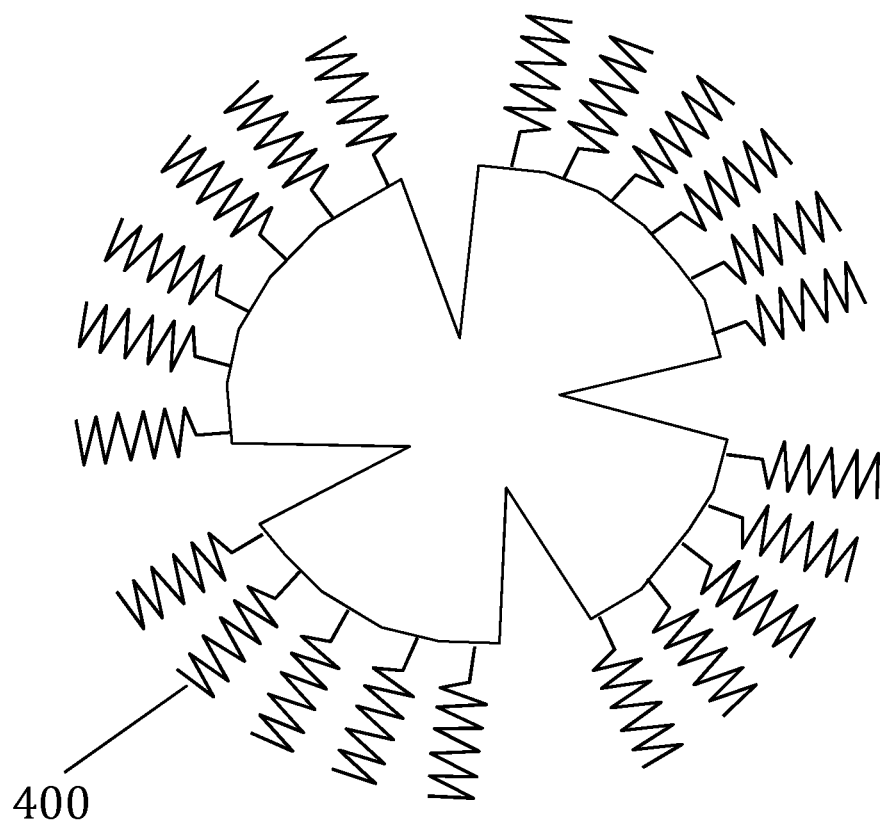
FIG. 4 shows a schematic of a porous support with surface functionalizing groups on the outer surface but not inside the pores.
Figure 5:
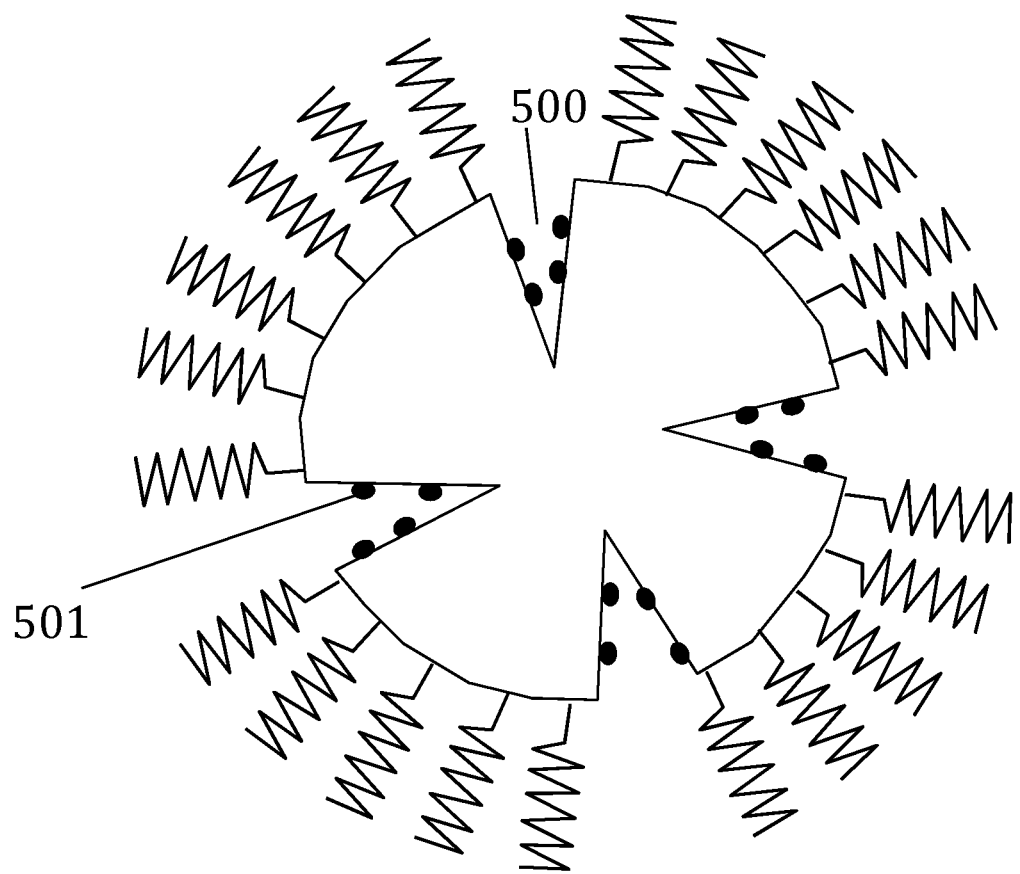
FIG. 5 shows a schematic of porous support with surface functionalizing groups on the outer surface but not inside the pores, further with photocatalyst nanoparticles formed in the pores but not on the outer surface.
Figure 6:
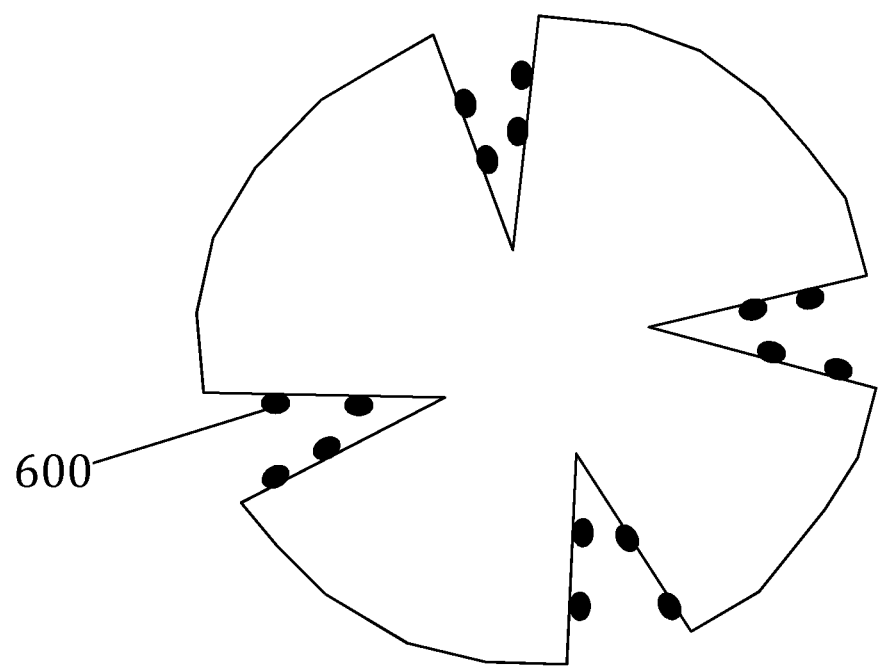
FIG. 6 shows a schematic of a porous support with surface functionalizing groups removed from on the outer surface, with photocatalyst nanoparticles remaining in the pores but not present on the outer surface.
Figure 7:
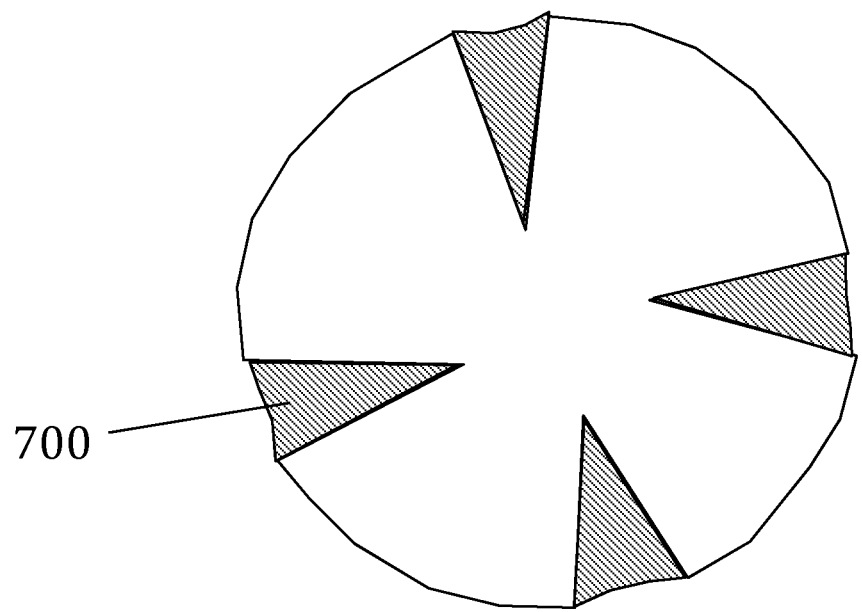
FIG. 7 shows a schematic of a porous support with the pores filled with a hydrophilic liquid.
Figure 8:
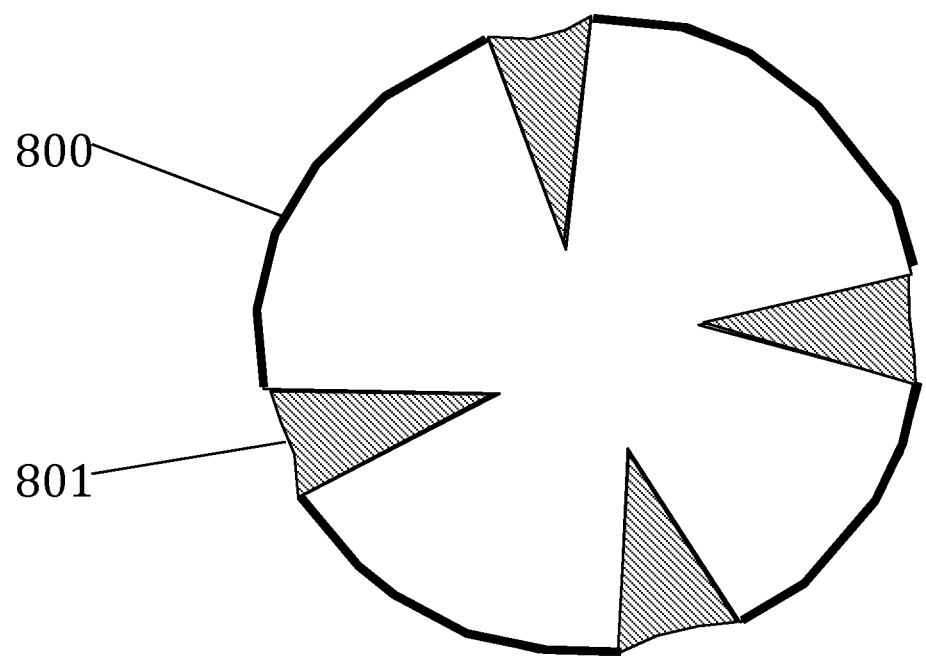
FIG. 8 shows a schematic of a porous support with the pores filled with a hydrophilic liquid and a hydrophobic layer formed on the outer surface but not in the pores.
Figure 9:
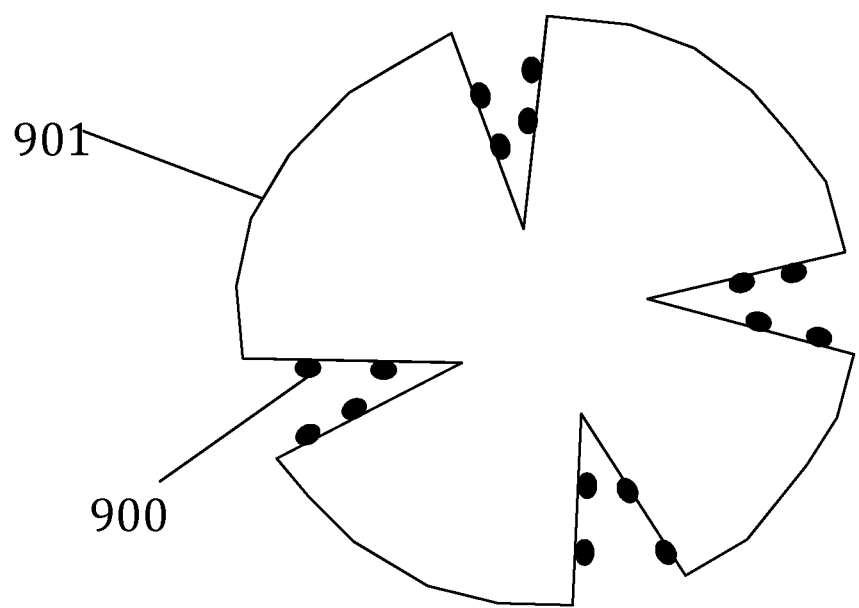
FIG. 9 shows a schematic of a porous support with the outer surface layer removed and photocatalyst nanoparticles remaining in the pores.

Monolithic composite photocatalysts can also be prepared such that the titania resides in the internal porosity of the porous support 300 and is not present on the external surface 301 (FIG. 3). Different, multistep loading strategies can be employed to achieve this hierarchical structure. The surface of the support may be functionalized with bulky or viscous moieties that cannot easily penetrate the porous network of the support 400 (FIG. 4). Examples of these ligands include long chain alcohols, long chain carboxylic acids, long chain phosphonic acids, and long chain alkoxysilanes or chlorosilane molecules. Impregnation of the photocatalyst precursor 501 will take place in the internal pores of the support 500 (FIG. 5), and high-temperature treatments can then be used to calcine the titania 600 and remove or decompose the organic species (FIG. 6). In a different approach, the pores of the support can be first filled with a highly adsorbed liquid, such as water, alcohol, dilute acid 700 (FIG. 7), allowing the surface of the support to be coated with hydrophobic groups 800 (FIG. 8). Photocatalyst precursors in hydrophilic solutions can then be infiltrated into the hydrophilic interior 801, and high-temperature treatments can be used to calcine the photocatalyst 900 and remove or decompose the deposited organic species 901 (FIG. 9).

The matrix containing the monolithic composite photocatalyst may be an article or stand-alone object or it may be a film deposited on a substrate. The inner portion of the monolithic composite photocatalyst may be exposed by removing a portion of the photocatalyst at the matrix surface or by adjusting the thickness of the matrix such that the monolithic composite photocatalyst extends above the matrix surface. Chemical etching or physical abrasion can be used to expose the internal titania at the matrix surface while maintaining the barrier separating the titania from the film matrix.

Figure 10:
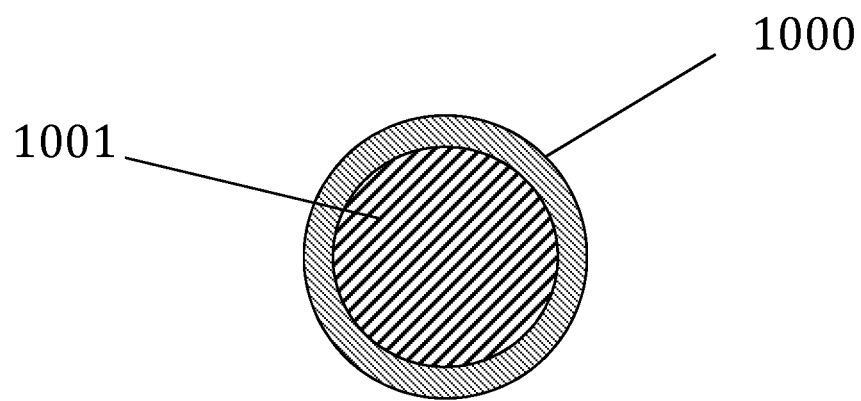
FIG. 10 shows a photocatalyst particle with a layer formed on the surface.

In order to reduce the degradation of a polymeric matrix by bulk titania (i.e., uncoated titania particles) or to further reduce the potential interaction of a monolithic composite photocatalytic particle with the surrounding organic matrix or organic containing matrix, a shell layer 1000 may be added to the photocatalytic particle 1001 (FIG. 10). This creates a core/shell structure in which the photocatalytic particle 1001 is the core and the layer on the outer surface of the particle 1000 is the shell. In this way, the generation of reactive oxygen species in proximity to the organic matrix can be reduced, thus reducing potential degradation of the surrounding matrix that could lead to loss of adhesion of the particles. This may also reduce degradation of mechanical or optical properties of the matrix extending from the particle sites, e.g., cracking of the matrix, reduced strength, reduced toughness, reduced transparency, etc. The shell layer may be any inorganic material, but may be an oxide or a nitride, for example $Al_2O_3$, $SiO_2$, $ZrO_2$, $HfO_2$, $Si_xN_y$, Si—C—O—N, or silicon.

Figure 11:
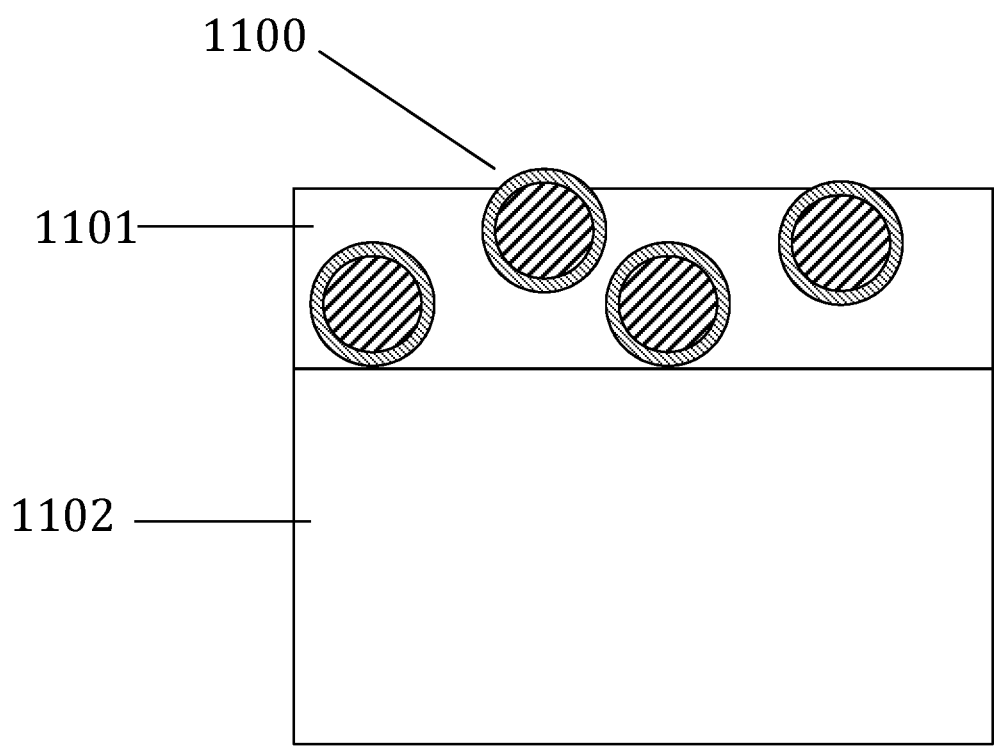
FIG. 11 shows photocatalyst particles with surface layers dispersed into a matrix to form a film.
Figure 12:
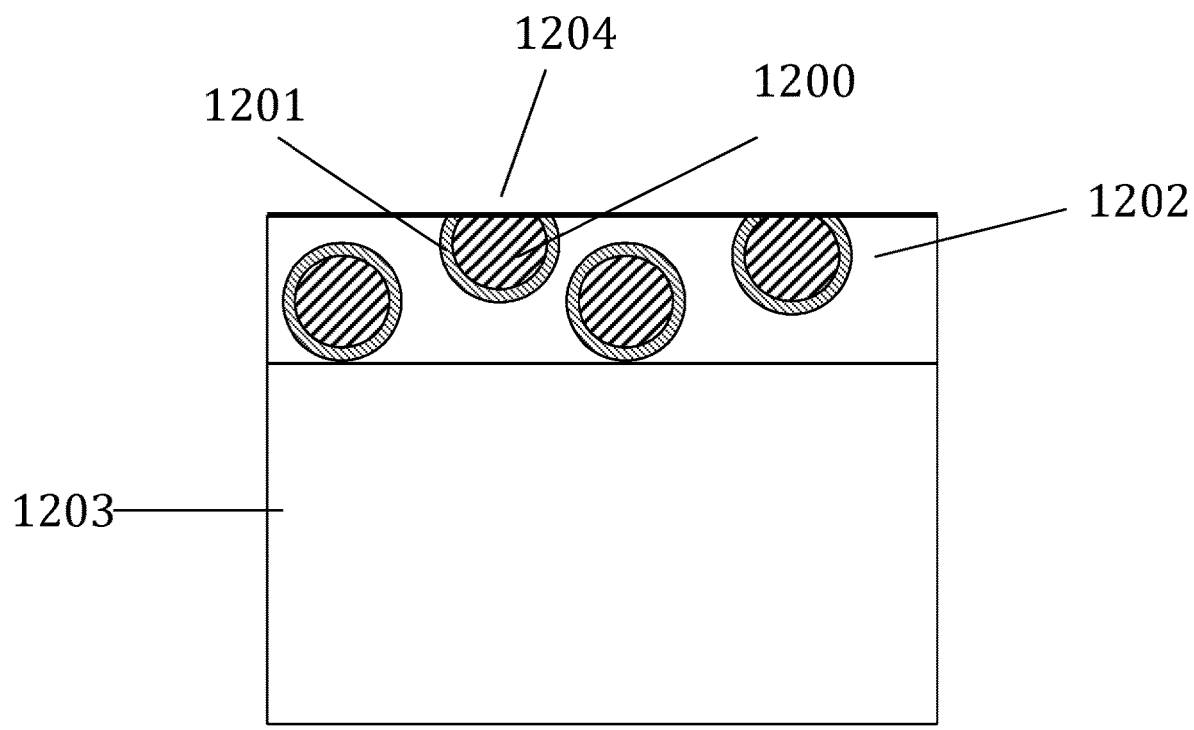
FIG. 12 shows the film of FIG. 12 with a portion of the outer surface removed to reveal the inside of the photocatalyst to the outer surface.
Figure 13:
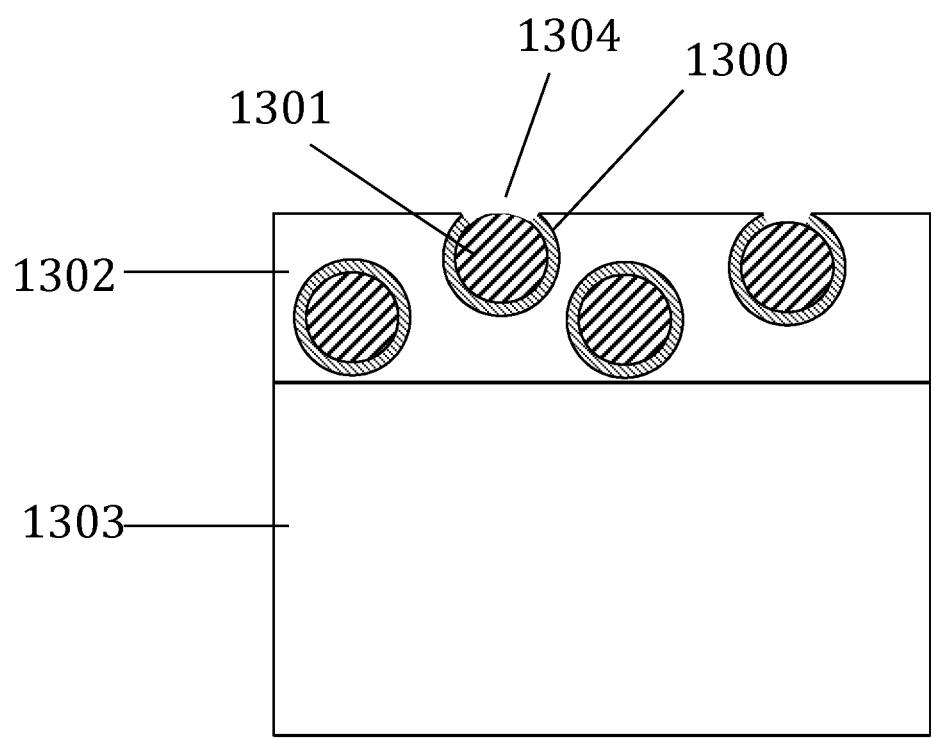
FIG. 13 shows the film of FIG. 12 with a portion of the surface layers on the photocatalyst particles removed to reveal the inside of the photocatalyst to the outer surface.

The shell layer may be applied to create a core-shell structure by wet chemical means, e.g., sol-gel or metalorganic deposition (MOD) or by a vapor means, e.g., chemical vapor deposition (CVD) or atomic layer deposition (ALD). For CVD, suitable precursors may be chosen for an $SiO_2$ shell, e.g., silanes, substituted silanes, amides, higher silanes (e.g., disilanes or substituted disilanes), or for an $Al_2O_3$ shell, e.g., amides, alkoxides, betadiketonates, and the like. For ALD, Si precursors may include 3-aminotriethoxysilane, halides, or siloxanes, including siloxo-halides; Al precursors include trimethylaluminum. In the case of ALD, the thickness of the shell may be controlled by the number of ALD cycles. An ALD cycle comprises a precursor dose, an intert purge, an oxidizer dose, and an oxidizer purge. Typical oxidizers include water, ozone, and oxygen plasma. ALD processes deposit 0.01-0.2 nm/cycle. The shell may be comprised of a thickness resulting from 1 to 100 ALD cycles, or 0.01-20 nm. Deposition temperatures for the shell materials described herein range from 50-300° C. In the case of CVD, the thickness of the coating is determined by the deposition temperature, precursor flux rate, and pressure. Deposition temperatures range from 150-650° C., deposition pressures range from 0.1-20 Torr, and precursor flow rates from 1-1000 μmol/min. Shell thicknesses may range from 0.1-20 nm. For an MOD or sol-gel approach, the shell may be from 1-100 nm in thickness. For sol-gel shells, the shell formed from alkoxide precursors, including methoxides, ethoxides, isopropoxides, and butoxides. For MOD, the precursors may be amides, betadiketonates, imides, or combinations of these ligands. The coated particles 1100 may then be incorporated into the polymer matrix 1101 (FIG. 11) and coated onto a substrate 1102 in the form of a film. It is desirable that the outer surface of the particle, i.e., that exposed at the matrix surface be free from the shell layer. This may be accomplished by abrasion of the surface using grinding, polishing, buffing, or bead blasting depending on the desired surface finish. Such a structure is shown in FIG. 12 where the photocatalyst particles 1200 with shell layers 1201 are embedded in a matrix 1202 to form a film on a substrate 1203 and have an inner portion 1204 of the photocatalyst exposed at the surface. Alternatively, the shell layer 1300 may be removing selectively from the 1301 photocatalytic particles once they are embedded in the matrix 1302 forming a film or layer on a substrate 1303, which also leaves the photocatalyst surface 1304 available for the desired photocatalytic reactions to occur (FIG. 13). Removal of the layer may be performed using a wet chemical etch that is selective toward the shell layer while leaving the photocatalytic core of the particle intact. For example, potassium hydroxide (KOH), buffered HF, or tetramethyl ammonium hydroxide (TMAOH) may be used to remove an $SiO_2$ shell layer while leaving a titania particle intact. KOH may be used to remove an $Al_2O_3$ shell layer. Dry (vapor) chemical etching or physical ion etching may also be used.

Vapors may include halides such as HF, HCl, and HBr. Physical ion etching may include Ar plasma or Ar ion-beams.

The shell layer approach may also be used with monolithic composite photocatalysts. In this case, selectivities of the etchants must be chosen to remove the coating where it is exposed above the matrix, but not the $TiO_2$ or the support material. For $SiO_2$ supported $TiO_2$, an alumina shell layer is desirable. Buffered hydrofluoric acid has good selectivity toward $Al_2O_3$ compared to $SiO_2$ (3:1 etch rate ratio (ERR)) and to $TiO_2$ (490:1 ERR). For $Al_2O_3$ supported $TiO_2$, a silica shell layer is desirable. 5% $H_3PO_4$ or a mixture of 3.8% TMAH-3.8% $NH_4OH$ in water may be used to remove the silica that is exposed above the polymer matrix, leaving the $TiO_2$ and $Al_2O_3$ intact.

A preferred embodiment employs photocatalytic illumination of the subject surface system in the visible spectral region, i.e., 400-700 nm wavelength, with light emitting diodes as the illumination source. There is a distinct advantage of using visible illumination in the 400-470 nm range, because of the efficiency of InGaN-based LEDs, and due to their high reliability and technological maturity. In some embodiments, all or some of the photocatalytic illumination may be in the 360-400 nm range (UV-A) and more preferably in the 380-400 nm range. These near UV illumination wavelengths may also be supplied by InGaN LEDs.

Another aspect of the invention relates to the geometry of the photocatalytic illumination, which will preferably be visible light photocatalytic illumination, such as from the back surface of a substrate, or via waveguide propagation through the photocatalytic containing matrix. Illumination and light-activation of the coatings on the hospital surfaces and hardware can occur from a number of different approaches, including from ambient room lighting, dedicated lighting under surfaces, scattered light, reflected light, and backlighting. Backlighting could be used, e.g., under table tops for continuous illumination. In this example, film thicknesses and photocatalyst concentrations are selected such that light can reach the upper surface in contact with patients and caregivers, providing the required antimicrobial action on the surface top.

For example, fused silica or silicone structures may be formed in the photocatalytic matrix, so as to effectively convey illumination to the surface sites where antimicrobial properties are desired. For back surface illumination, these structures may have an optical transmittance characteristic with directional components normal to the surface. For edgewise illumination, these structures may employ light guiding parallel to the surface. In either case, shapes such as focusing devices or microlenses may be formed into the matrix material to convey or intensify illumination to the surface sites. Combinations of such structures may be utilized to deliver adequately uniform photocatalytic illumination from LED point sources or synthesized linear LED sources. In some embodiments, a combination of photocatalytic illumination may include a combination of back surface and front surface (i.e., ambient) illumination.

Photocatalytic nanocrystals in the 10-25 nm range do not cause optical scatter for visible wavelengths, with wavelengths on the order of 10× the particle sizes. In general, photocatalyst-containing matrix materials will optically appear as a homogenous material with a refractive index predicted by effective medium theory, e.g., the law of mixtures. Matrix materials with low optical absorption are preferred to increase flexibility in design of the photocatalytic illumination scheme. Low optical absorption matrix materials may be either transparent, in the case of low optical scattering, or opaque, in the case of a high degree of incoherent optical scattering.

The invention includes monolithic integration of the subject photocatalytic surfaces near the surface of a solid-state light emitting device such as an LED or OLED. In this context the LED devices may be individually packaged die, multiple die modules, LED lamps (e.g., conventional light bulbs, MR-16s, etc.), lighting fixtures and luminaires. For LED packages and modules, the photocatalytic material would be back surface illuminated in these integrated devices. The subject surface may be either front or back surface illuminated, depending on technical and aesthetic aspects of the device design.

One such invention relates to purification of surfaces of medical tools, kitchen counter top surfaces, or other implements or everyday items, either during use or when in storage.

Visible-light-activated photocatalysts may be employed to impart antimicrobial properties to a variety of touch surfaces if the photocatalytic coatings exhibit high durability as provided by the present invention. Examples include touch screens, smart phone covers, elevator buttons, light switches, door knobs, table tops, machine switches, keyboards, and wheels for rolling carts or mobile equipment. These items may be illuminated by ambient light or by lights provided internally for various functionality, e.g., backlighting of a smart phone screen, indicator lighting in switches, etc. The light source may be optionally programed to come on at intervals. The light source may be an LED with a wavelength in the range of 365 nm to 415 nm, or more preferably 405-415 nm.

Another implementation may be the use of visible light activated photocatalytic materials in wound dressings. In this application, antimicrobial properties may be achieved without the use of antibiotics or materials toxic to the body. The dressing may be lighted externally or may have an in internal light source. An example of the latter is a photoluminescent layer in proximity to the photocatalytic layer in the bandage. The illuminating layer could be a two component mixture that is activated by breaking a barrier layer between the two materials that react to form light.

The Inventions summarized above are described and illustrated in several examples or embodiments, which are not intended to be limiting on the scope of the inventions.

$TiO_2$ NCs were prepared from titanium isopropoxide and oleic acid in a typical solvothermal process. Following isolation, the oleic acid ligands on the $TiO_2$ NCs were exchanged for triethoxyoctylsilane ligands. These nanocrystals were dissolved in a small amount of toluene and added to a mixture of tetraethylorthosilicate in isopropanol. The concentration of nanocrystals is adjusted by modifying the NC to silica precursor ratio. The amount of solvent controls the film thickness. A small amount of dilute HCl was added to initiate condensation reactions. The solution was stirred for 30 min and then spin-coated to a transparent film that was annealed at 120° C. Depending on the application, the $TiO_2$ NCs can be doped with lanthanides, including cerium, during the solvothermal reaction to shift the bandgap of the NCs to longer wavelengths such that they can be activated with visible light. Alternatively, metals (in the form of coatings or NCs) can be added to the nanocrystals to enhance electron-hole separation. The liquid matrix-NC composite can be spray-coated directly onto hospital furniture or instruments. Alternatively, the liquid matrix-NC composite can be printed on rolls of polyethylene terephthalate (PET). The coated plastic can then be applied to hospital furniture in patient and operating rooms.

Figure 14:
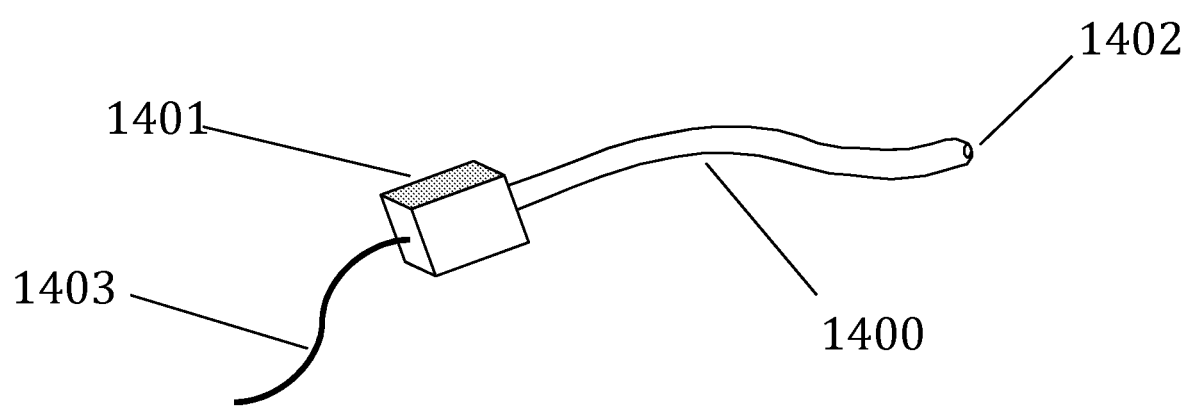
FIG. 14 shows a schematic of a catheter that is internally illuminated.
Figure 15:
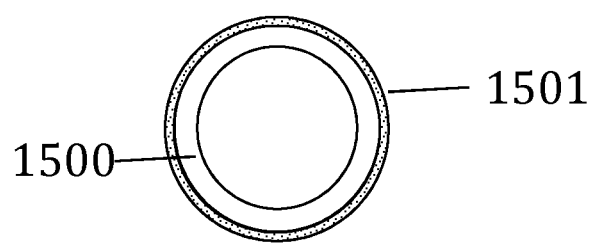
FIG. 15 shows a schematic of the cross section of the catheter in FIG. 14 with a photocatalytic surface.

Another device useful in medical applications is disclosed. Catheters are subject to accumulation of biofilms on their surfaces, especially when kept in place for extended times. Examples include venous and urinary catheters. The current art for self-sterilizing catheters utilizes silver particles or photocatalytic particles that must be activated by UV light. The former approach may lead to excessive silver absorption by the body, with negative consequences. The current photocatalytic approach is deficient in that it requires UV light, which is harmful to body tissue. Although illumination of a catheter may be performed prior to insertion, the antimicrobial effect decays quickly. A visible light activated photocatalyst would allow in-situ illumination. The illumination may be provided by a suitable light transmitting fiber, preferably one that emits radially along its entire length, thus providing even illumination along the length of the catheter or through the catheter material using the catheter itself as a light guide. FIG. 14 shows a catheter 1400 that is connected to housing with a light source 1401 located away from the distal end 1402. The light source may be battery operated or have an external power supply via a lead 1403 to the light source housing. The surface of the catheter 1500 has visible light active titania photocatalyst 1501 (FIG. 15) at the surface or in a region from the surface toward the axial center of the catheter. Illumination may be continuous or intermittent. Intermittent illumination may be programed with an electronic device to optimize the frequency and duration of the illumination for optimal biofilm prevention. The light source may be a visible light emitting LED with a broad or narrow spectral output. The preferred spectral output is tuned to the adsorption properties of the photocatalyst. The catheter is made of a flexible optically transmissive material, e.g. a light transmissive polymer. The visible light activated photocatalyst may be distributed throughout the catheter or applied to its surface. Methods to produce the catheter include co-extrusion of the visible light activated photocatalyst, application of a monomer containing the catalytic particles to the surface, or treating the surface of the catheter to generate an adhesive character. In the latter cases, a polymerizing step may be used to cross link the surface. Preferred surfaces are hydrophobic polymers, which may comprise the matrix that contains the visible light activated photocatalyst.

The catheter may also be fitted with an integrated or proximate sensor to detect body chemistry indicating conditions favorable for microbial growth. For example, a pH sensor may detect acidity of basicity or urine that indicates the propensity for developing an infection. The illumination may be modulated based on the indications of the sensor.

Figure 16:
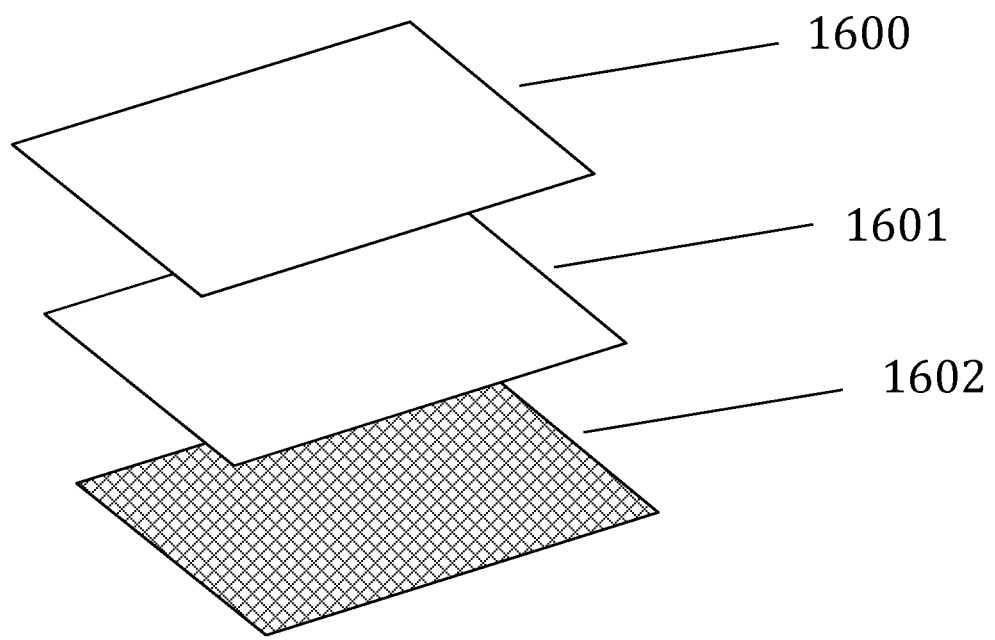
FIG. 16 shows a schematic of a mutilayer wound dressing with visible light activated photocatalytic layer.

Certain wounds may provide higher likelihoods of surgical site infection, especially those involving sutures that may penetrate the skin. A wound dressing with a photocatalytic antimicrobial action may be used to minimize the viability of bacteria at the wound site. It is desirable that the wound dressing be inexpensive and disposable. Such a wound dressing (FIG. 16) would be comprised of multiple layers. The layer farthest from the skin 1600 is a protective layer, that may be transmissive to moisture and air. An intermediate layer 1601 provides illumination, from a luminescent material that may be activated when the bandage is applied. The illuminating layer is in proximity to a layer 1602 closest to the wound that is made of a material transparent to light of the illuminating wavelength and covered or impregnated with photocatalytic particles of any type described in this invention. A light transparent material may be disposed between the layer closest to the wound and the illuminating layer. The illuminating layer may be an encapsulated two part mixture that when a membrane between the two parts is broken by flexing, the mixture emits light for a period of time. The illuminating layer may have through-holes to allow the passage of moisture from the skin without exposing the skin to the light emitting materials inside the membrane. The period of time may be from 1-24 hours and the light wavelengths may be from 400-425 nm. Once illuminated, the layer closest to the skin provides reactive oxygen species that create an antimicrobial action.

One application for in vivo use of the subject invention is to create a chemically active oxidizing surface at the end of a fiber optic probe inside the body. In this case the optical exit surface of the probe would have engineered photocatalytic properties as discussed above, and the illumination would therefore be from the back surface. The probe end could be brought into proximity or into contact with tissue or an implanted surface, and the active surface could be employed for disrupting biofilms, contributing active oxygenating species, modifying tumors etc.

One possible use of the subject invention is for in vivo delivery of photocatalytic illumination for the purposes of modifying biochemistry inside the body, and especially to disrupt the growth and deleterious effects of biofilms. Biofilms are a serious problem in a significant fraction of implanted devices such as hip joints, knee joints, implant hardware (i.e., titanium screws, rods and plates) and defibrillators. Visible or ultraviolet illumination may be delivered to the subject photocatalytic surface on an implanted device, through a sheathed fiber optic bundle that is considered standard for bio-imaging and delivery of other useful illumination. The fiber optic may be a single fiber, or a bundle (either imaging or non imaging type) and may be shared with imaging functions that are commonplace in surgical procedures. The illumination may be directed to exposed area of the implanted device, i.e., 'front surface" illuminated. The illumination may also be provided to the back surface of the relevant surface, through a pre-engineered optical port with geometric or lightguiding optics to deliver the illumination to interior surfaces that are prone to biofilm formation.

Additive manufacturing, also known as 3-d printing is a highly relevant solid fabrication process that may beneficially incorporate photocatalytic technologies of the subject invention. Additive manufacturing typically involves a laminar formation of layers with various layer dimensions, via robotic delivery of pastes or liquids in a controlled pattern that are subsequently hardened via thermal and/or optical processing to form a defined shape. It may include additive or subtractive formation of layers over the entire 3-d structure near the final fabrication steps. The subject photocatalytic materials, suspended or dissolved in an organic or inorganic paste or liquid, may be introduced anywhere on individual or multiple laminar elements as the 3-d structure is built up. A preferred embodiment is use of organic matrix materials such as epoxies, polyurethanes and silicones. The 3-d printing process may thus distribute these component materials selectively along the edges of a layer, for example. An overcoating photocatalytic active material may also be added via spraying, 3-d printing or other liquid distribution means, thereby dispensing the liquid in a controlled pattern over a pre-existing structure and, after hardening, forming a final matrix in a defined shape with a photocatalytic surface.

The mechanical stiffness, hardness, elasticity and other properties may also be controlled by varying the incorporation amounts of other additives, including oxide or carbide nano particles or micro particles, introduction of carbon fibers, varying amounts of the constituent organic matrix materials, etc.

Optical elements may also be formed in the interior of the 3-d printed structures, for distribution of photocatalytic illumination from external sources. These structures may be comprised of light guides (typically circular, elliptical or rectangular cross section), or lenses. These transmissive structures may preferably be formed from silicone. Reflective elements may also be formed in the interior of the 3-d printed solid.

Illumination interface ports may also be fabricated at the edges of the subject solid material during fabrication.

LEDs or micro LEDs may also be incorporated in the interior of the 3-d printed solid with photocatalytic surface properties, and it is evident that this type of structure may also be fabricated with a combination of manufacturing techniques that may include 3-d printing.

One valuable application for the subject 3-d printed solids is as in vivo implant materials, such as synthetic cartilage to replace the meniscus in the knee, or for other body parts such as tendons.

Antimicrobial surfaces of the present invention will be utilized in a range of healthcare, industrial and residential environments that typically rely on liquid cleaners to remove or reduce residual pathogens on surfaces. These subject surfaces will be physically and chemically robust in the presence of such liquid cleaners, which typically are applied by cloth or fiber-based wipes or mops, and in some cases via misters, that distribute nebulized liquids, typically hydrogen peroxide ($H_2O_2$) throughout a room and onto the surfaces. Photocatalytic surfaces of the present invention are intended to work with existing liquid cleaning protocols.

Standard commercial antimicrobial liquid cleaners utilize one of several active chemicals that kill or disrupt viruses, bacteria and spores. These constituents include chlorinating species such as sodium chlorite or sodium hypochlorite, hydrogen peroxide, or peracetic acid as the active ingredients, along with a range of other inert ingredients.

One aspect of the subject photocatalytic surface systems is the use of modified cleaners that include, in addition to the standard constituents, photocatalytic enhancing species, which are agents to enhance photocatalytic antimicrobial efficacy. In this case the complementary antimicrobial properties of the surface are greater than with either the cleaning liquids or photocatalytic surfaces by themselves. The subject photocatalytic surfaces for such cleaners may include either composite photocatalyst-matrix systems, or continuous photocatalyst thin films formed by methods such as ALD.

One route to enhance photocatalytic effects is via Fenton reactions, which utilize iron or other ions to dramatically increase the concentration of active OH radicals on a surface, and hence improve the antimicrobial properties. The archetypal Fenton reaction is:

$$Fe^{2+}+H_2O_2 \rightarrow Fe^{3+}+HO.+OH^-$$

In this reaction Fe is a catalyst under acidic conditions, and peak efficiency is for pH~3. In this case $Fe^{+2}$ (Iron(II)) is oxidized by hydrogen peroxide to $Fe^{+3}$ (Iron(III)), forming a hydroxyl radical (a neutral form of the hydroxide ion) and a hydroxide ion in the process. $Fe^{+2}$ may be provided in a solution of $FeSO_4$ or $FeNO_3$, and $Cu^{2+}$ and other transition metal ions may also be utilized.

The hydroxyl radical and hydroxide ion are extremely strong oxidizers, and generation of these species on the surfaces of the subject invention will increase the reactivity and resulting antimicrobial effects or other oxidizing effects (e.g., for dissociation of VOCs) of the photocatalytic surface.

In this case the reactant $H_2O_2$ may be generated by the photocatalytic effect on the $TiO_2$ (titania) nanoparticle surfaces:

$$TiO_2+h\nu \rightarrow TiO_2(h^++e^-)$$

Where hv is an incident photon with adequate energy to create electrons e− and electron holes h+. The photocatalytic effect thus forms oxidative species at the $TiO_2$ surface, including:

$$h^++H_2O \rightarrow H^++.OH$$

$$2h^++2H_2O \rightarrow 2H^++H_2O_2$$

$$H_2O_2 \rightarrow 2.OH$$

Photocatalytic formation of $H_2O_2$ would therefore provide a Fenton reactant that would react with applied solutions of iron salts. Alternatively, the $H_2O_2$ may be supplied externally as photocatalytic enhancing species in a cleaning agent. In those cases the subject liquid cleaning formulations would also have utility in the absence of a photocatalytic surface.

Another related mechanism of photocatalytic enhancing cleaning liquids is via the photo-Fenton effect, which has several orders of magnitude greater energy efficiency for generation of active oxygen, relative to titania based photocatalysis:

$$Fe(OH)^{2+}+h\nu \rightarrow Fe^{2+}+HO.$$

One source of iron ions for the photo-Fenton effect may be from aqueous solutions of iron oxylate, $FeC_2O_4$. Optical absorption of the resulting ferrioxylate complex $[(Fe(C_2O_4)_3]$ can extend from UV through 550 nm wavelength, and hence this photo-driven reaction is an efficient source of hydroxyl radicals and resulting antimicrobial effects. Other photo-Fenton ligands may also be employed.

Photocatalytic enhancing cleaning agents would therefore incorporate combinations of standard aqueous based disinfectants with one or more photocatalytic enhancing species in solution, including:

Sources of iron or other transition metal ions that would react or catalyze reactions at active photocatalytic surface sites typically along with moisture. These could include simple iron or other transition metal salts in solution at molarities in the range of 500 nM to 50 mM.

Hydrogen peroxide, $H_2O_2$, with concentrations in the 0.1% to 7% range.

Sources of hydrogens ions H+ to establish an acidic environment at the photocatalyst surface, e.g., acetic acid, peracetic acid, citric acid, caffeic acid, citric acid, ascorbic acid, or tartaric acid, resulting in pH in the range of 2-6.5.

These species, in combination with trace adsorbed moisture, would enhance photocatalytic effects subsequent to the liquid or mist cleaning process. These photocatalytic enhancing cleaning liquids would be topically applied via wipes or mobs, jet spray, misters or ultrasonic nebulizers.

A sample of monolithic composite photocatalyst with an anatase titania phase greater than 80%, BET surface area of 100 m²/g, pore size in the 6-40 nm range, and pore volume in the 0.4-0.7 cc/g range was ground in a mortar and pestle (75 mg). The powder was added to 1.5 mL water, and the slurry was sonicated for 40 minutes. A glass substrate (1"×1.5") was prepared by a dilute nitric acid wash followed by a piranha etch wash, rinsed with water, and dried in a stream of nitrogen. The monolithic composite photocatalyst in water was drop-cast onto the surface of the substrate, and the sample was placed into an oven at 120° C. for 2 hours. The substrate was then heated to 300° C. for 1 hour and cooled.

Figure 17:
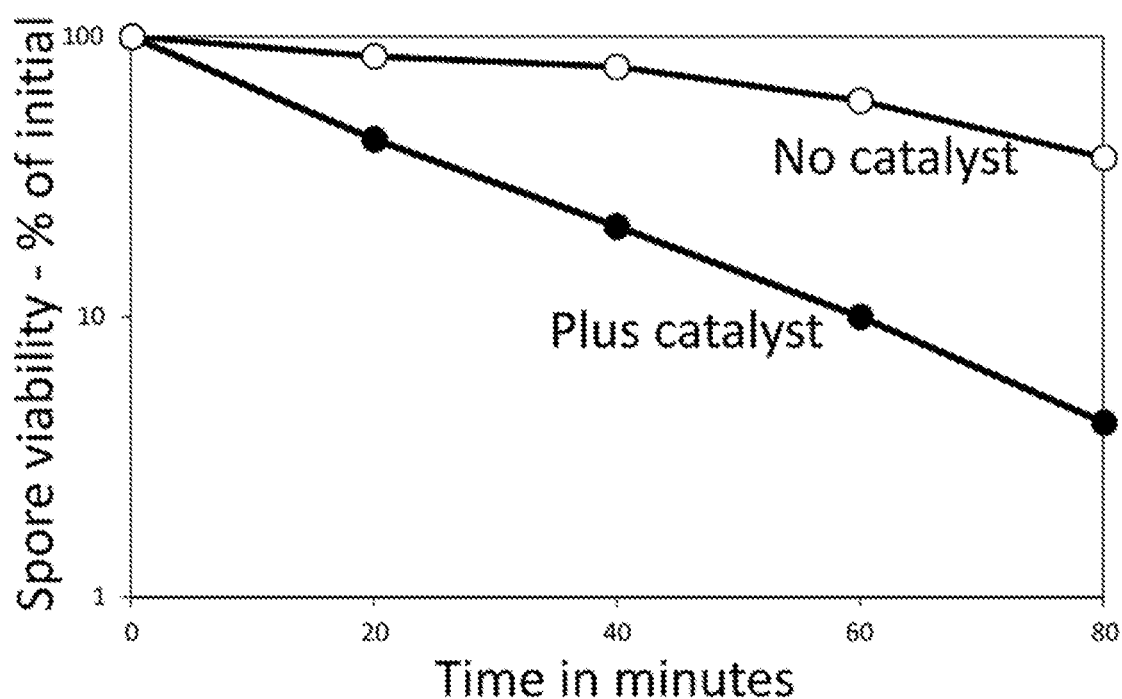
FIG. 17 shows the sporicidal activity of a thin film of a powdered monolithic composite photocatalyst (dark circle) using 365 nm irradiation. The sporicidal activity of a thin film of a powdered support without photocatalyst (open circles) is included for comparison.

Highly purified dormant spores of a 168 strain of *Bacillus subtilis*, PS533, which carries a plasmid providing resistance to kanamycin (10 μg/mL), were suspended in water at ca. $1.5 \times 10^8$ colony forming units (CFUs)/mL. Approximately 1.5 mL of this suspension was applied to the prepared slides. The slides with the spores were then exposed at 23° C. to 365 nm irradiation approximately 6 cm from a single LED operating at a radiant flux of 2750 mW. At various times aliquots (ca. 20 μL) of the irradiated samples were diluted 1/10 in water and then serially diluted further. 10 μL aliquots of various dilutions were then spotted in duplicate in a grid on rich medium (L broth) agar plates containing 10 μg/mL kanamycin. After liquid was absorbed into the plates, they were incubated 16-36 h at 30-37° C., ensuring that individual colonies never got large enough to run together. However, no colonies appeared after ca 30 h. Finally, colonies were counted for irradiated samples with and without the active photocatalyst, and CFUs, and thus the percentage of spore viability at various irradiation times, were calculated. An example of spore killing with and without (support only) active photocatalyst is shown in FIG. 17.

The subject invention may be embodied in the forgoing examples and embodiments that are by no means restrictive, but intended to illustrate the invention. Different embodiments and examples given previously may be freely combined.

What is claimed is:

1. A photocatalytic surface system, comprising a UV-A or visible light activated titania-based photocatalytic material in contact with a matrix material, wherein the photocatalytic material consists of a mixture of photocatalytic surfaces and non-photocatalytic surfaces, there being a plurality of contact interfaces between the matrix material and the photocatalytic material, wherein less than 90 percent areal density of each of the plurality of contact interfaces is between the matrix material and a photocatalytic surface of the photocatalytic material, the remainder of the contact interface being between the matrix material and a non-photocatalytic surface of the photocatalytic material.

2. The photocatalytic surface system of claim 1, wherein the photocatalytic material is a colloidal photocatalytic nanocrystal capped with non-photocatalytic solubilizing ligands.

3. The photocatalytic material of claim 2, wherein the solubilizing ligand is selected from the group consisting of alkoxysilanes, phosphonic acids, carboxylic acids, alcohols, and sulfonic acids.

4. The photocatalytic material of claim 2, wherein the colloidal photocatalytic nanocrystals are 2-15 nm in diameter.

5. The photocatalytic surface system of claim 1, wherein the photocatalytic material comprises a monolithic composite photocatalyst support having pores, the pores having photocatalytic surfaces dispersed within them, the photocatalytic surfaces covering no more than 90 percent areal density of the surface of the monolithic composite photocatalyst support, the monolithic composite photocatalyst support being formed of a non-photocatalytic material, together forming a monolithic composite photocatalyst.

6. The photocatalytic surface system of claim 5, wherein the monolithic composite photocatalyst comprises photocatalytic particles forming the photocatalytic surfaces, wherein the photocatalytic particles incorporate a core-shell geometry, wherein the shell layer is non-photocatalytic, further wherein the shell layer has been at least partially removed at the matrix surface to enable greater antimicrobial efficacy.

7. The photocatalytic surface system of claim 6, wherein the shell layer is comprised of silica, alumina, zirconia, hafnia, $Si_xN_y$, Si—C—O—N, or silicon.

8. The photocatalytic surface system of claim 5, wherein the external surface of the monolithic composite photocatalyst is greater than 50% free of active photocatalyst nanoparticles by percent areal density, wherein photocatalyst is present in the interior pores of the monolithic composite photocatalyst, wherein a portion of the monolithic composite photocatalyst has been at least partially removed at the matrix surface to enable greater antimicrobial efficacy.

9. The photocatalytic surface system of claim 1, wherein the photocatalytic material is bulk titania particles coated with a non-photocatalytic shell layer, wherein the shell layer has been at least partially removed above the matrix surface to enable greater antimicrobial efficacy.

10. The surface system of claim 9, wherein the shell layer is comprised of silica, alumina, zirconia, hafnia, $Si_xN_y$, Si—C—O—N, or silicon.

11. The photocatalytic surface system of claim 1, wherein the matrix is comprised of polyurethanes, epoxies or silicones.

12. The photocatalytic surface system of claim 11, wherein the matrix contains inorganic nanocrystals, particles or fibers that modify the mechanical properties of the matrix, thereby increasing the resistance of the matrix to mechanical wear.

13. The photocatalytic surface system of claim 1, wherein the matrix is comprised of silicon oxide, aluminum oxide, titanium oxide, or refractory oxide forming precursors.

14. A method of manufacturing the photocatalytic surface system of claim 1, the method comprising: mixing the photocatalytic material into a paste or liquid thereby dispersing the photocatalytic material in the paste or liquid, dispensing the paste or liquid in a controlled pattern, hardening the paste or liquid to form a solid having a defined shape based on the controlled pattern, thereby suspending the photocatalytic material in the matrix material, exposing at least a portion of the photocatalytic material at a surface of the matrix thereby forming a photocatalytic surface system, and exposing the photocatalytic surface system to UV-A or visible light, thereby stimulating photocatalytic activity.

15. A liquid cleaning agent for cleaning a solid surface, comprising the photocatalytic surface system of claim 1, comprising the UV-A or visible light activated titania-based photocatalytic material in contact with a matrix material, the photocatalytic surface system formed into particles, that provides photocatalytic enhancing species to the surface.

16. The liquid cleaning agent of claim 15, wherein the liquid cleaning agent is applied by cloths, fibrous implements, mops, sprays, jets, misters or nebulizers.

17. The liquid cleaning agent of claim 15, wherein the photocatalytic enhancing species enable Fenton or photo-Fenton reactions.

18. The liquid cleaning agent of claim 15, wherein the photocatalytic enhancing species includes Fe.

19. The liquid cleaning agent of claim 15, wherein the cleaning agent combines photocatalytic enhancing species and halide containing species.

20. The liquid cleaning agent of claim 15, wherein the solid surface contains photocatalytic antimicrobial materials.

\* \* \* \* \*